United States Patent [19]

Bates et al.

[11] Patent Number: 4,656,289

[45] Date of Patent: Apr. 7, 1987

[54] 1,3-DIBENZYL-4-HALOHEXAHYDRO-1H-THIENO[3,4-D]IMIDAZOL-2(3H)-ONE INTERMEDIATES

[75] Inventors: Hans A. Bates, Stony Brook; Stuart Rosenblum, West Hempstead, both of N.Y.

[73] Assignee: The Research Foundation of State Univ. of New York, Albany, N.Y.

[21] Appl. No.: 664,505

[22] Filed: Oct. 25, 1984

[51] Int. Cl.$^4$ ............................................. C07D 495/04
[52] U.S. Cl. ................................................. 548/303
[58] Field of Search .......................................... 548/303

[56] References Cited

U.S. PATENT DOCUMENTS 2,489,234  11/1949  Goldberg et al. .................. 548/303

OTHER PUBLICATIONS

Lavielle et al., *J. Amer. Chem. Soc.*, 100, No. 5, pp. 1558–1563, (1978).
Isaka et al., *Yakugaku Zasshi*, 88, No. 8, pp. 1068–1073 (1968).
Morrison and Boyd, *Organic Chemistry*, 4th Edit., pp. 466 and 488, (1983).
March, *Advanced Organic Chemistry*, 2nd Ed., p. 341 (1977).
House, *Modern Synthetic Reactions*, 2nd Ed., pp. 415–421 (1972).

*Primary Examiner*—Henry R. Jiles
*Assistant Examiner*—Kurt G. Briscoe
*Attorney, Agent, or Firm*—Omri M. Behr

[57] ABSTRACT

Novel synthetic routes to (3aα,6aα)-1,3-dibenzyl hexahydro-1H-thieno[3,4-d]imidazol-2(3H)-one 5,5-dioxide, a known intermediate in the synthesis of biotin are provided.

A novel synthetic route from this intermediate to biotin is also disclosed.

2 Claims, 4 Drawing Figures

2
FIG. 2
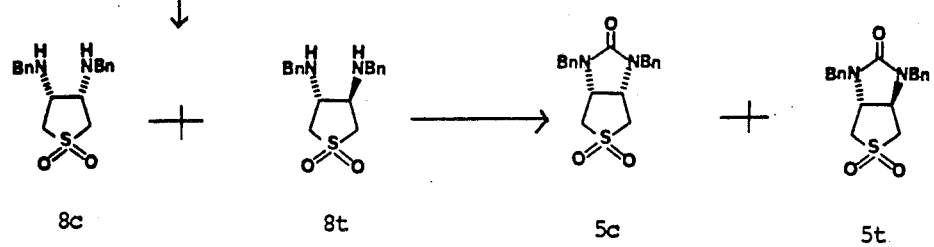
FIG. 3
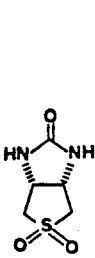
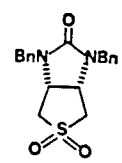

1,3-DIBENZYL-4-HALOHEXAHYDRO-1H-THIENO[3,4-D]IMIDAZOL-2(3H)-ONE INTERMEDIATES

BACKGROUND OF THE INVENTION

Biotin, which is variously known as (3aα,4β,6aα)-hexahydro-2-oxothieno[3,4-d]imidazole-4-pentanoic acid or vitamin H is a natural product originally isolated from egg yolk and liver. A stereo specific synthesis of d-biotin (Confalone, et al., *JACS*, 97, 5936 (1975) is known but is not commercially viable. Present commercial production is believed to depend an early patented process disclosed in U.S. Pat. No. 2,489,232. It would be desirable to provide a high yield process using inexpensive starting materials. One total synthetic route is disclosed by Lavielle, et al. (*JACS*, 100, 1558 (1978)).

An important intermediate in the synthesis of biotin is (3aα,6aα)-1,3-dibenzylhexahydro-1H-thieno[3,4-d]imidazol-2(3H)-one 5,5-dioxide whose synthesis is reported by Ohba, et al., *Agr. Biol. Chem.*, 38, 2431 (1974). A synthesis of the dibenzyl derivative thereof is reported by Kotake, et al., *Chemistry Letters*, 1073 (1976). The problem with the Kotake synthesis is that the first stage yields a mixture of two products which are only separable by column chromatography. The major portion is the trans isomer which is not the desired product. While the conversion of the desired cis-isomer with phosgene affords the (3aα,6aα)-1,3-dibenzylhexahydro-1H-thieno[3,4-d]imidazol-2(3H)-one 5,5-dioxide in quantitative yield, the intermediate chromatographic separation step constitutes a substantial barrier in the way of industrial use of the process. It would therefore be desirable to modify the Kotake process in such a way as to either avoid the problem of separation of isomers or at least provide isomeric products which are separable by more industrially viable procedures such as differential crystallization.

SUMMARY OF THE INVENTION

The present invention provides three different routes to the desired (3aα,6aα)-1,3-dibenzylhexahydro-1H-thieno[3,4-d]imidazol-2(3H)-one 5,5-dioxide from readily available starting materials. It also provides a route for the conversion of this product through the corresponding (3aα,6aα)-1,3-dibenzylhexahydro-1H-thieno[3,4-d]imidazol-2(3H)-one (disclosed by Kotake) to the corresponding 4-chlorothienoimidazolone which is convertable either to the corresponding 4-oxo-(3aα,6aα)-1,3-dibenzylhexahydro-1H-thieno[3,4-d]imidazol-2(3H)-one a known intermediate on one synthetic route to biotin.

BRIEF DESCRIPTION OF THE DRAWINGS

FIGS. 2 and 3 show different synthetic routes to the aforesaid (3aα,6aα)-1,3-bidenzylhexahydro-1H-thieno[3,4-d]imidazol-2(3H)-one 5,5-dioxide.

DESCRIPTION OF THE PREFERRED EMBODIMENTS

Figure 1:
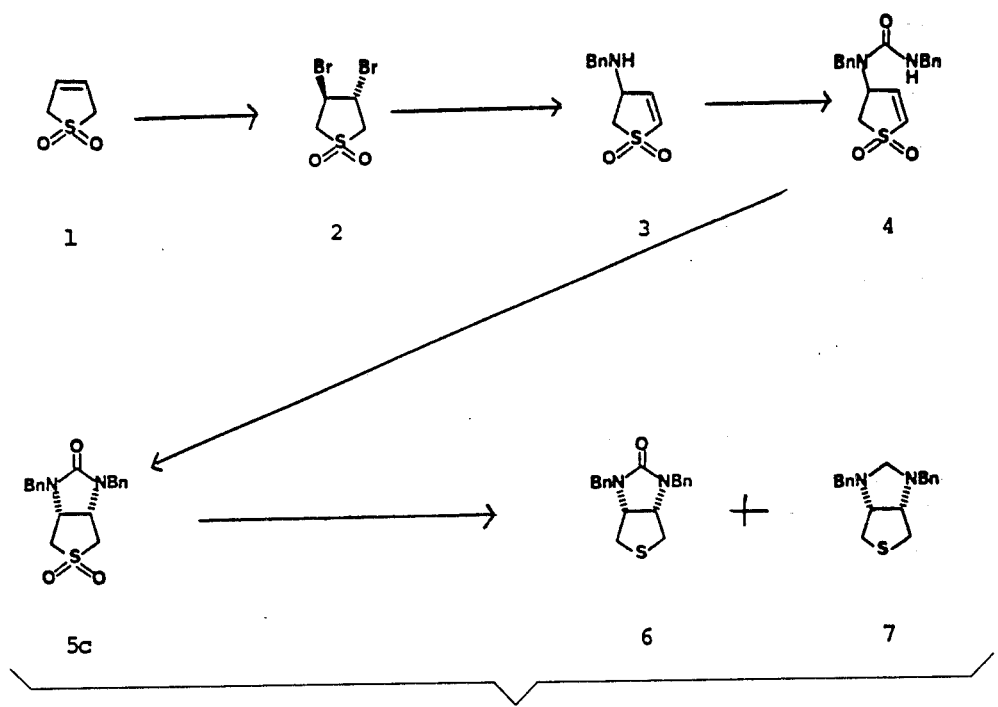
FIG. 1 shows one synthetic route to the 1,3-dibenzyl-(3aα,6aα)-1,3-dibenzylhexahydro-1H-thieno[3'4-d]imidazol-2(3H)-one 5,5-dioxide and its conversion to the (3aα,6aα)-1,3-dibenzylhexahydro-1H-thieno[3,4-d]imidazol-2(3H)-one.

In the process of FIG. 1 the starting material 2,5-dihydrothiophene-1,1-dioxide (1) is brominated in a suitable halohydrocarbon solvent by the action of bromine. The addition is complete in about 4 hours and heating under reflux for a further 2 hours completes the reaction. The product trans-3,4-dibromotetrahydrothiophene 1,1-dioxide (2) precipitates in good yield and is separated by filtration.

The trans-3,4-dibromotetrahydrothiophene 1,1-dioxide (2) is taken up in a lower alkanol (1 to 5 carbon atoms) suitably methanol and a 5X molar excess of a tertiary amine suitably triethylamine added thereto. There is then added a suitable primary amine. By suitable primary amine is meant an amine which will, in the latter stages of the synthetic sequence, yield an imidazole carrying a protecting group on the nitrogen of the imidazole moiety which will be resistant to the subsequent steps of the synthetic sequence.

There may be used as the protecting moiety lower alkyl groups, suitably containing 1 to 5 carbon atoms, or aryl lower alkyl groups preferably phenyl lower alkyl groups wherein the alkyl moiety similarly has 1 to 5 carbon atoms. Especially preferred mainly for reasons of availability and cost, is the benzyl group. The reaction mixture is maintained at between −20 to 65 degrees C., preferably at around 0 degrees C. during the addition of the tertiary amine. It is also maintained in this range during the addition of the primary amine although in this case an operating temperature of about 20 degrees C. is preferred. After addition is complete the reaction mixture is stirred for from about 12 to about 24 hours, the solvent removed under reduced pressure, the product treated with aqueous sodium carbonate and extracted into a suitable water-immiscible polar organic solvent, such as dichloromethane. Evaporation of this latter solvent under reduced pressure yields the desired product (3) in good yield. It should be noted however that this product is somewhat unstable and should be immediately processed in the next stage.

The thus obtained N-protected-2,3-dihydro-3-thiophenamine 1,1-dioxide (3) is taken up in a water-immiscible organic solvent, suitably a hydrocarbon solvent such as benzene and treated with a small excess (suitably from about 30 to about 60 mole percent excess) of an alkyl or aralkyl isocyanate. Thus where the protecting group on compound (3) is benzyl, it is desirable to utilize benzylisocyanate. The reacton may be carried out at from about 20 to about 100 degrees C., it being preferred however to carry out the reaction under reflux, that is to say, at the higher end of the range. The time for completion of the reaction will of course depend upon the temperature utilized, that is between 10 and 48 hours the reaction generally being complete under reflux conditions at about 80 degrees C. after about 10 hours.

Evaporation of the solvent under reduced pressure yields the corresponding N-(protected aminocarbonyl)-N-protected-2,3-dihydro-3-thiophenamine 1,1-dioxide (4), wherein, in the preferred mode, the protecting groups are benzyl. This new product may be purified but such purification is not necessary and the thus produced urea (4) may be directly utilized in the next stage. The urea (4) is taken up in a small amount of a polar solvent, such as a lower alkanol, suitably methanol or ethanol, and water (about 10 times the volume of alkanol). The mixture is then allowed to stand at ambient temperature or heated, suitably up to about 100 degrees C. for about 5 to about 20 minutes, and cooled to ambient temperature to yield the (3aα,6aα)-1,3-dibenylhexahydro-1H-thieno[3,4-d]imidazole-2(3H)one 5,5-dioxide (5c) in subtantially quantitative yield.

In accordance with the procedures of Kotake, this thiophane dioxide (5c) may be reduced to the corresponding tetrahydrothiophene (6) with lithium aluminum hydride in about 60% yield.

In the procedure of FIG. 2, 3,4-dibromotetra hydrothiophene 1,1-dioxide (2) was taken up in methanol and benzylamine (10 times excess) was added thereto in a modification of the procedures of Kotake and Ohba. Afer subsidance of the initial exothermic reaction, the mixture was heated under reflux for between 4 to about 8 hours, the solvent removed under reduced pressure and the residue washed with dilute acid to yield a 65:35 mixture of the trans- and cis-isomers (3aα,6aβ)- and (3aα,6aα)-1,3-dibenzylhexahydro-1H-thieno[3,4-d]imidazol-2(3H)-one 5,5-dioxide (8t) and (8c).

This product, can, if desired, be separated by chromatography on silica gel. This separation procedure however is not suitable for commercial scale preparations and the mixture of cis-trans isomers is used without further purification in the next stage.

The mixture of trans- and cis-diamines (8t and 8c) were taken up in an inert solvent suitaably dichloromethane and a substantial excess, i.e., approximately 300% excess of a tertiary amine, suitably triethylamine. The reaction mixture is held at between about −95 and about +40 degrees C., suitably around 0 degrees C. and a solution of phosgene in the aforementioned solvent is added thereto. An excess of phosgene suitably about a 200% excess is utilized. The reaction mixture is held within the aforementioned temperature range. The volatiles are removed under reduced pressure and the residue dissolved in water at 50 degrees C. The quenching mixture is cooled to ambient temperature and extracted with the aforementioned solvent. Washing with acid and dilute base yields a mixture of the trans- and cis-isomers namely (3aα,6aβ)- and (3aα,6aα)-1,3-dibenzylhexahydro-1H-thieno[3,4-d]imidazol-2(3H)-one 5,5-dioxide (5t),(5c).

The cis-isomer may be readily crystallized from hot chloroform as a white crystalline solid. The residue of this crystallization includes the trans-isomer which may be purified by recrystallization from hot benzene/hexane to yield the trans-isomer (5t).

As shown in FIG. 3 sequence, (3aα,6aα)-hexahydro-1H-thieno[3,4-d]imidazol-2(3H)-one 5,5-dioxide (9) prepared in accordance with the procedure of Ohba, may be alkylated by reaction with a large excess (between 40 and 60 times excess) of an alkyl or phenylalkyl halide. The alkyl moiety suitably contains 1-5 carbon atoms, and the halo group may be bromo or chloro. It has been found suitable to employ benzyl bromide in the presence of moderately strong (5 to 10M) aqueous alkali, suitably sodium hydroxide or potassium hydroxide in a slightly lesser excess, (i.e. between 5 and 20 times excess). The reactants are taken up in water, vigorously stirred and heated under reflux for from about 18 to about 30 hours to yield, after extraction, the corresponding dibenzyl derivative (6) as a residual oil which, upon treatment with a solvent such as ether yields the desired product as a crystalline precipitate.

Compound (6) may be converted into biotin in approximately 68% yield (literature) by the method of Lavielle, et al., (JACS, 100, 1558, 1978).

It should be noted however that the Lavielle preparation of (6) which claims a 60% literature yield overall was found in our hands to yield but 30%.

Figure 4:
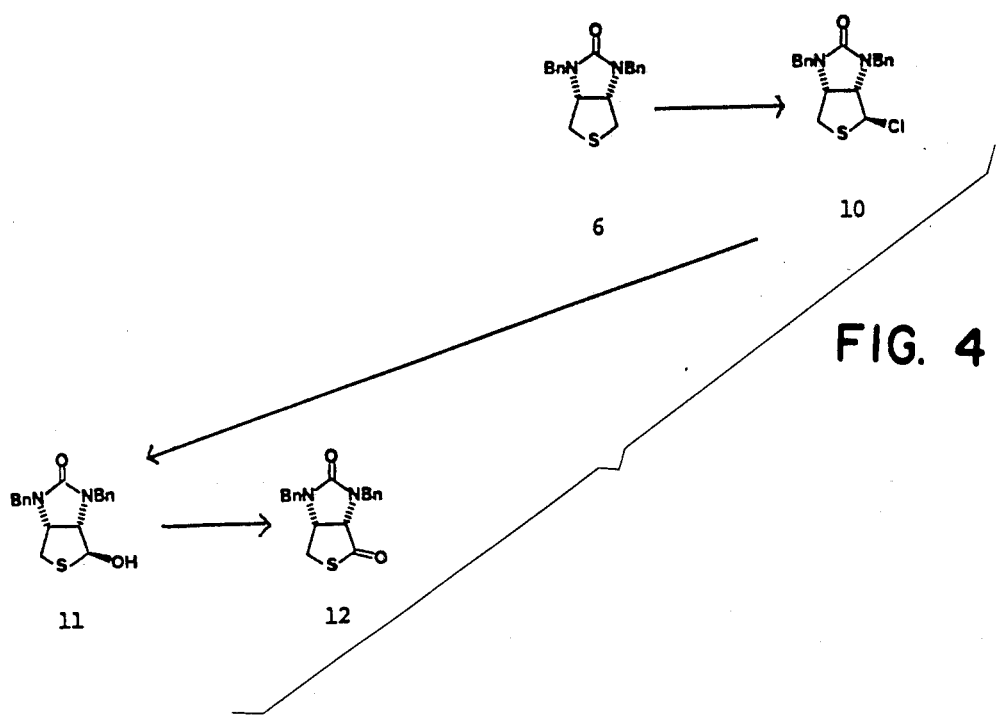
FIG. 4 shows the synthetic sequence of the conversion of the (3aα,6aα)-1,3-dibenzylhexahydro-1H-thieno[3,4-d]imidazol-2(3H)-one to a known intermediate in the synthesis of biotin.

The intermediate (6) may be converted into a biotin intermediate as is shown in the scheme of FIG. 4.

In this procedure the dibenzyl (3aα,6aα)-1,3-dibenzylhexahydro-1H-thieno[3'4-d]imidazol-2(3H)-one (6) is converted into the corresponding 4β-chloro compound (10) which itself serves as an intermediate for the synthetic pathway.

Compound (6) is reacted with a small excess of a mild halogenating agent such as an N-halosuccinimide such as N-chlorosuccinimide at ambient temperature in a halohydrocarbon or hydrocarbon solvent, suitably an aromatic hydrocarbon solvent such as benzene, under an inert dry atmosphere, suitably a nitrogen atomosphere. After from about 4 to about 8 hours an additional small excess, suitably up to about a 25% excess of additional N-chlorosuccinimide is added and the reaction mixture quenched with water followed by extraction with a suitable water-immiscible solvent such as dichloromethane. The organic phase is separated to yield the 4-chloro compound as a crystalline solid in substantially quantitative yield.

The 4β-halo, suitably chloro, compound (10) is readily hydrolyzed in substantially quantitative yield by treatment with excess aqueous alkali in a water-miscible organic solvent suitably dioxan. While the reaction may be carried out from between 0 to 100 degrees C. it is generally preferred to carry it out at substantially ambient temperature for a period of from about 1 to about 5 days. After completion of the reaction the residue is taken up in water and extracted with a suitable water immiscible organic solvent suitably a halogenated hydrocarbon solvent such as dichloromethane. Evaporation of the extracting solvent yields the desired 4-hydroxy compound (11) as a crystalline substance, again in substantially quantitative yield.

Oxidation to the corresponding dione is carried with an extremely mild oxidising agent. A suitable class of such agents comprise dimethyl sulfoxide in the presence of an acid halide or anhydride of a carboxylic acid. Specifically, there may be named acetic anhydride, trifluoroacetic anhydride, and oxalic anhydride. This grouping is purely exemplary and in no way as limiting.

The 4-hydroxy compound (11) was taken up in dry chloroform and added to a dry solution of ethanol free chloroform containing approximately equal amounts of excess (approximately 6 times excess) of the oxidising agent of choice, for example, trifluoroacetic anhydride and dimethylsulfoxide. The reaction was commenced at a bath temperature of approximately −60 degrees C. and is allowed to warm slightly to about −50 degrees C. After about 2 hours the reaction appears to be complete. The reaction mixture was permitted to warm to about 0 degrees C. and quenched with water. Extraction with chloroform yields, upon evaporation of the solvent, a product which upon purification by chromatography on silica gel affords approximately 50% starting material and the corresponding 2(3H),4-dione (12) as a white crystalline solid in approximately 75% yield based upon recovered starting material.

This dione (12) is convertable into biotin in accordance with U.S. Pat. Nos. 2,489,232 and 2,489,235.

EXAMPLE 1

Trans-3,4-Dibromotetrahydrothiophene 1,1-dioxide (2)

A solution of 2,5-dihydrothiophene 1,1-dioxide (1) (59 g, 500 mmol) in chloroform (200 mL) was refluxed beneath a condenser fitted with a drying tube. Bromine (26 mL, 507 mmol. 101 mol %) in chloroform (26 mL) was added over a period of 4 hr, and the mixture was refluxed 2 hr more. A precipitate formed toward the end of the addition. The after the mixture was cool, the precipitate (119 g, 86% yield) was collected by filtration, and allowed to dry: m.p. 138°–141° C. $^1$H NMR (CDCl$_3$) δ 3.7 (4H, m, CH$_2$SO$_2$), 4.75 (2H, m, CHBr).

EXAMPLE 2

N-Benzyl-2,3-dihydro-3-thiophenamine 1,1-dioxide (3)

To a solution of 3,4-dibromotetrahydrothiophene 1,1-dioxide (2) (13.90 g, 50.0 mmol) in methanol (250 mL) at 0° C. was added triethylamine (36 mL, 26.1 g, 259 mmol, 518 mol %). After 20 min., benzylamine (5.5 mL, 5.39 g, 50.3 mmol, 101 mol %) was added, and the mixture was stirred at 20° C. for 18 h. The solvent was removed by rotary evaporation, and the product was extracted five times from saturated sodium carbonate solution into dichloromethane. The organic phase was dried and rotary evaporated to afford the somewhat unstable product as an oil (8.36 g, 75% yield). $^1$H NMR (CDCl$_3$) δ 2.4 (1H, s, NH), 3.03 (1H, dd, CHOS$_2$), 3.43 (1H, dd, CHSO$_2$), 3.82 (2H, s, CH$_2$Ph), 4.20, (1H, m, CHN), 6.62 (2H, m, CH=CH), 7.25 (5H, s, arom); MS, m/e (relative intensity) 223 (1), 222 (3), 106 (85), 91 (100), 65 (13); IR (neat), 3360, 3110, 1615 cm$^{-1}$.

In accordance with the above procedure but where, in place of benzylamine, there is utilized methylamine, ethylamine, n-propylamine, t-butylamine, phenylethylamine, phenylpropylamine or phenylisopentylamine, there are obtained the corresponding N-lower alkyl- and N-phenyl lower alkyl-2,3-dihydro-3-thiophenamine 1,1-dioxides.

EXAMPLE 3

N-(Benzylaminocarbonyl)-N-Benzyl-2,3-dihydro-3-thiophenamine 1,1-dioxide (4)

Benzylisocyanate (2.26 g, 17.0 mmol, 135 mol %) was added to a mixture of amine 3 (2.80 g, 12.6 mmol) in a benzene (75 mL). After 10 hr of reflux, the solution was cooled and filtered, and the solvent was evaporated from the filtrate to afford the crude product (3.29 g, 74% yield). A portion was purified by column chromatography on silica gel with dichloromethane-ethyl acetate. $^1$H N NMR (CDCl$_3$) δ 1.7 (1H, s, NH), 3.02 (1H, dd, CHSO$_2$), 3.65 (1H, dd, CHSO$_2$), 4.4 (4H, m, CH$_2$Ph), 4.95, (1H, m, CHN), 6.57 (2H, m, CH=CH), 7.23 (10H, s, arom).

EXAMPLE 4

(3aα,6aα,)-1-3-Dibenzylhexahydro-1H-thieno[3,4-d]imidazol-2(3H)-one 5,5-dioxide (5c)

Crude urea (4) (1.984 g, 5.57 mmol) was dissolved in methanol (5 mL) and water (45 mL) and briefly heated, then cooled. The crystalline product (1.796 g, 91% yield) was collected by filtration: m.p. 176°–9° C., lit. m.p. 184° C. IR 1695 cm$^{-1}$ MS, m/e (relative intensity) 356 (12), 265 (51), 201 (7), 132 (31), 91 (100); 1H NMR (CDCl$_3$) 2.98 (4H, m, CHSO$_2$), 4.10 (2H, m, CHN), 4.21 (2H, d, CH$_2$Ph), 4.66 (2H, d, CH$_2$Ph), 7.27 (10H, s, arom); $^{13}$C NMR (CDCl$_3$) δ 46.25 (t), 52.35 (t), 53.02 (d), 127.73 (d), 128.85 (d), 137.60 (s), 160 (s). Anal. Calcd. for C$_{19}$H$_{20}$N$_2$O$_3$S: C, 64.02; H, 5.655. Found: C, 63.99; H, 5.77.

EXAMPLE 5

(3aα,6aα, Dibenzylhexahydrothieno[3,4-d]imidazol-2(3H)-one (6)

The sulfone (5c) (736 mg, 2.07 mmol) was suspended in anhydrous ether (15 mL) and cooled to 0° C. A freshly prepared solution of lithium aluminum hydride in anhydrous ether (22.9 mg/mL, 7.5 mL, 172 mg, 4.52 mmol, 219 mol %) was added at 0° C. with vigorous stirring over a period of five minutes. After an additional 15 min of stirring of 0° C., the precipitate, originally, globular, became granular. The reaction mixture was stirred at 20° C. for 15 min, cooled to 0° C., and quenched with water (0.17 mL), 15% NaOH (0.17 mL), and water (0.51 mL). The insoluble aluminum salts were removed by filtration and rinsed with ether (2×20 mL). The ether was evaporated from the combined filtrate to afford the crude product which was redissolved in benzene (10 mL) and extracted three times with 1M HCl. The benzene layer was dried and evaporated. The residue was dissolved in a minimum quantity of dichloromethane and ether was added to afford the product (402 mg, 60% yield), spectroscopically and chromatographically identical to an independently prepared sample m.p. 108°–110° C. lit. m.p. 110°–111° C., $^1$H NMR (CDCl$_3$) δ 2.70 (4H, m, CHS), 3.98 (2H, m, CHN), 4.17 (2H, d, CH$_2$Ph), 4.75 (2H, d, CH$_2$Ph), 7.27 (10H, s, arom).

The aluminum salts were further extracted three times with dichloromethane to afford the starting material (140 mg, 19% recovery) which could be recrystalized from hot chloroform and recycled.

The combined HCl phase was made basic with NaOH and extracted three times with dichloromethane. The organic phase was dried and evaporated to afford over reduced product (7) (90 mg, 14% yield): m.p. 48°–50° C. MS. m/e (relative intensity) 310 (12), 309 (47), 219 (4), 91 (100), $^1$H NMR (CDCl$_3$) δ 2.55 (4H, m, CHS), 3.02 (1H, d, J=5 Hz, NCHN), 3.42 (2H, m, CHN), 3.64 (4H, s, CH$_2$Ph), 3.94 (1H, d, J=5 Hz, NCHN), 7.25.

EXAMPLE 6

In accordance with the above procedures of Examples 4 and 5 in place of the 1,1-dioxide (4) there are utilised as starting materials the other products of Example 3. There are obtained the corresponding cis-di lower alkyl- and phenyl lower alkylhexa hydrothieno[3,4-d]imidazol-2(3H)-ones and the corresponding 5,5-dioxide analogs.

EXAMPLE 7

Trans- and Cis-N,N-Dibenzyltetrahydrothiophenediamine 1,1-dioxide (8t and 8c)

A modification of literature procedures was utilized. 3,4-Dibromotetrahydrothiophene 1,1-dioxide (2) (14.0 g, 50.3 mmol) was dissolved in methanol, and benzylamine (53.8 g, 503 mmol, 1000 mol %) was added. After the initial exothermic reaction subsided, the mixture was refluxed for 6 hr, and the methanol was evaporated. The residue was treated with 1M HCl (240 mL, 240 mmol, 447 mol % pH=7.3) and the product was extracted four times into dichloromethane. The dichloromethane phase was washed with saturated sodium carbonate solution, and dried. Evaporation of the solvent left a residue of the product and benzylamine. This residue was twice triturated with boiling hexanes then cooled to afford a 65:35 mixture of the trans- and cis-diamines (14.0 g, 84% yield) as a white solid.

Part of the mixture (200 mg) was separated by chomatography on silica gel (2.5×15 cm, 40–63 micron) with ethyl ether-benzene-pyridine (50:50:1). The faster eluting compound (69 mg) was the cis diamine (8c): m.p. 105°–6° C., lit. m.p. 111°–111.5° C. $^1$H NMR (CDCl$_3$) δ 2.0 (2H, s, NH), 2.9–3.4 (6H, m), 3.54 (4H, AB-quartet, CH$_2$Ph), 7.13 (10H, s, arom).

The slower eluting compound (111 mg) was the trans diamine (8t): m.p. 106°–7° C., lit. m.p. 109°–110.5°, 114°–5° C. $^1$H NMR (CDCl$_3$) δ 1.8 (2H, s, NH), 2.5–3.4 (6H, m), 3.58 (4H, s, CH$_2$Ph), 7.13 (10H, s, arom).

EXAMPLE 8

(3aα,6aβ,)- and (3aα,6aα)-1,3-Dibenzylhexahydrothieno[3,4-d]imidazol-2(3H)-one 5,5-dioxide (5t and 5c)

A mixture of trans- and cis-diamines (8t) and (8c) (3.54 g, 10.7 mmol) was dissolved in dichloromethane (45 mL) and triethylamine (4.4 mL, 31.5 mmol, 294 mol %) at 0° C. A solution of phosgene in dichloromethane (5.5 mL of 3.85 mg/mL, 2.12 g, 2.14 mmol, 200 mol %) was added. After 15 min at 0° C., the phosgene and dichloromethane were evaporated. The residue was dissolved in water at 50° C. After 5 min, the water mixture was cooled and extracted with three portions of dichloromethane. The organic phase was washed with 1M HCl and saturated sodium carbonate, dried, and evaporated to afford a mixture of the cis and trans products (3.66 g, 96% yield). The mixture was recrystallized from hot chloroform (25 mL) to afford the cis isomer (5c) (1.38 g, 36% yield) as a white crystalline solid: m.p. 176°–9° C., lit. m.p. 184° C. The same compound was obtained when the pure cis diamine was treated with phosgene.

The chloroform was evaporated from a filtrate, and the residue was recrystallized from hot benzene-hexanes (2:1) to afford the trans isomer (5t) (2.0 g, 53% yield) as a white solid: m.p. 144°–7° C.; IR 1730 cm$^{-1}$; MS m/e (relative intensity) 356 (6), 265 (19), 201 (6), 132 (14), 91 (100); $^1$H NMR (CDCl$_3$) δ 3.0 (6H, m), 4.16 (2H, d, CH$_2$Ph), 4.61 (2H, d, CH$_2$Ph), 7.26 (10H, s, arom); $^{13}$C NMR (CDCl$_3$) δ 49.35 (t) 57.03 (t), 58.57 (d), 128.24 (d), 128.52 (d), 128.88 (d), 135.62 (s), 162.62 (s); Anal. Calcd for C$_{19}$H$_{20}$N$_2$O$_3$S: C, 64.02; H, 5.665. Found C, 64.09; H, 5.71.

The same compound was obtained when the pure trans diamine was treated with phosgene.

EXAMPLE 9

(3aα,6aα,)1,3-Dibenzylhexahydrothieno[3,4-d]imidazol-2(3H)-one 5,5-dioxide (5c)

(3aα,6aα)Tetrahydrothieno[3,4-d]imidazol-2(3H)-one 5,5-dioxide (9) (500) mg, 2.85 mmol) was dissolved in water (8.5 mL.) Aqueous 8.4M NaOH (3.4 mL, 28.5 mmol, 1000 mol %) and benzyl bromide (12.4 mL, 19.5 g, 114 mmol, 4000 mol % 4) were added with vigorous stirring and the mixture was refluxed for 24 h. After cooling, the product was extracted with three portions of dichloromethane. The organic phase was dried and evaporated. The residual oil was treated with ether, and the white precipitate (963 mg, 95%) was collected by filtration: m.p. 174°–6° C.; lit. m.p. 184° C. IR 1695 cm$^{-1}$ MS, m/e (relative intensity) 356 (12), 265 (51), 201 (7), 132 (31), 91 (100); $^1$H NMR (CDCl$_3$) δ 2.98 (4H, m, CHSO$_2$), 4.10 (2H, m, CHN), 4.21 (2H, d, CH$_2$Ph), 4.66 (2H, d, CH$_2$Ph), 7.27 (10H, s, arom); $^{13}$C NMR (CDCl$_3$) δ 46.25 (t), 52.35 (t), 53.02 (d), 127.73 (d), 128.85 (d), 137.60 (s), 160 (s). Anal. Calcd. for C$_{19}$H$_{20}$N$_2$O$_3$S: C, 64.02; H, 5.655. Found: C, 63.99; H, 5.77.

In accordance with the above procedures of but where, in place of benzyl bromide, there is utilized methyl chloride, bromide, or iodide, ethyl chloride, bromide, or iodide, n-propyl chloride, bromide, or iodide, t-butyl chloride, bromide, or iodide, phenylethyl chloride, bromide, or iodide, phenylpropyl chloride, bromide, or iodide or phenylisopentyl chloride, bromide, or iodide, there are obtained the corresponding cis- dilower alkyl- and phenyl lower alkylhexahydrothieno[3,4-d]imidazol-2(3H)-one 5,5-dioxide.

EXAMPLE 10

(3aα,4β,6aα)-1,3-Dibenzyl-4-chlorohexahydro-1H-thieno[3,4-d]imidazol-2(3H)-one (10)

N-Chlorosuccinimide (97.9 mg, 0.0736 mmol, 106 mol %) was added over 5 min to a stirred solution of (3aα,6aα,)-1,3-Dibenzylhexahydrothiopheno[3,4-d]imidazol-2(3H)-one (6) (225.3 mg, 0.694 mmol) in benzene at 15° C. under nitrogen. After 6 hr at 15° C., additional N-chlorosuccinimide (15.4 mg, 0.116 mmol, 17 mol %) was added. After an additional 1 hr, water (5 mL) was added, the layers were separated, and the aqueous phase was extracted three times with dichloromethane. The organic phase was dried and evaporated to afford the chloro compound (10) (245.2 mg, 0.683 mmol, 98% yield) as a white solid. M.p. 108°–109° C. NMR (CDCl$_3$, 300 MHz) 3.00 (1H, dd, J=1.3, 12.7, CH$_2$S), 3.18 (1H, dd, J=3.6, 12.7, CH$_2$S), 3.96 (1H, dd, J=1.2, 7.0, NCH), 4.01 (1H, ddd, J=1.3, 3.6, 7.0, NCH), 4.01 (1H, ddd, J=1.3, 3.6, 7.0, NCH), 4.21 (1H, d, J=15.4, CH$_2$Ph), 4.32 (1H, d, J=15.4, CH$_2$Ph), 4.61 (1H, d, J=15.4, CH$_2$Ph), 4.78 (1H, d, J=15.4, CH$_2$Ph), 5.25 (1H, d, J=1.19, CH—Cl), 7.26–7.34 (10H, m, arom); $^{13}$C NMR (CDCl$_3$, 75 MHz); 158.0, 136.7, 136.6, 128.2, 128.0, 127.9, 127.7, 72.7, 72.4, 60.0, 47.3, 46.2, 36.41; mass spectrum, m/e (relative intensity) 360 (13), 358 (M$^+$, 29), 323 (4), 91 (100); IR (CHCl$_3$) 3020, 2980, 1700, 850 cm$^{-1}$.

Anal. Calcd. for C$_{19}$H$_{19}$N$_2$OSCl: C, 63.59; H, 5.34; N, 7.81. Found: C, 61.71; H, 5.34; N, 7.78.

In accordance with the above procedure, but where in place of N-chlorosuccinimide, there is used N-bromo succinimide, there is obtained the corresponding 4-bromo imidazolone.

EXAMPLE 11

(3aα,4β,6aα)-1,3-Dibenzylhexahydro-4-hydroxy-1H-thieno[3,4-d]imidazol-2(3H)-one (11)

Aqueous 1M NaOH (1.3 mL, 1.3 mmol, 250 mol%) was added to a solution of (3aα,4Nβ,6aα)-1,3-Dibenzyl-4-chlorohexahydro-1H-thieno[3,4-d]imidazol-2(3H)-one (10) (190.3 mg, 0.530 mmol) in dioxane (1.5 mL). After 3 days at 22° C., the solvent was evaporated, the residue was dissolved in water and the solution was extracted three times with dichloromethane. The organic layer was dried and the solvent was evaporated to afford the product (11) (166.3 mg, 92% yield) as a white crystalline solid. M.p. 122°–125° C. ¹H NMR (CDCl₃) 2.52 (1H, br. s, OH), 2.75 (1H, m, CH₂S), 3.01 (1H, dd, CH₂S), 3.94 (1H, br. d, J=8.0, NCH), 4.14 (1H, ddd, NCH), 4.13 (1H, d, J=15.1, CH₂Ph), 4.68 (1H, d, J=15.1, CH₂Ph), 4.68 (1H, d, J=15.1, CH₂Ph), 5.12 (br. s, CH—O); 7.25 (10H, m, arom); ¹³C NMR (CDCl₃ 159.5, 128.82, 128.19, 128.10, 136.91, 84.32, 47.44, 46.83, 69.30, 63.61, 30.22; mass spectrum, m/e (relative intensity) 340 (M⁺, 15), 187 (56), 91 (100).

Anal. Calcd. for C₁₉H₂₀N₂O₂: C, 67.03; H, 5.92; N, 8.23. Found: C, 67.39; H, 5.36; N, 8.21.

EXAMPLE 12

(3aα,6aα)-1,3-Dibenzylhexahydro-1H-thieno[3,4-d]imidazol-2(3H),4-dione (12)

To trifluoroacetic anhydride (0.14 mL, 207 mg, 1.0 mmol, 615 mol %) in ethanol-free chloroform (washed three times with water, dried over calcium chloride and distilled, 0.10 mL) at −60° C. (bath temperature) was added DMSO (0.080 mL, 88 mg, 1.13 mmol, 700 mol %) was added over 5 min. After 5 min, a solution of (3aα,4β,6aα)-1,3-Dibenzylhexahydro-4-hydroxy-1H-thieno[3,4-d]imidazol-2(3H)-one (11) (54.6 mg, 0.161 mmol) in CHCl₃ (0.10 mL) was added via syringe. Additional chloroform (0.30 mL) was added to dissolve the precipitate and the bath temperature was increased to −50° C. The reaction appeared to stop after 2 hr. After 6 hr, the reaction was warmed to 0° C., water (2 mL) was added, and the mixture was extracted three times with chloroform. The organic layers were dried and the solvent evaporated to afford crude product (51.8 mg) which was purified by flash chromatography on silica gel (hexane-ethyl acetate 50:50) to afford recovered starting material (25.9 mg) and (3aα,6aα)-1,3-Dibenzyl-hexahydro-1H-thieno[3,4-d]imidazol-2 (3H),4-dione (12) (20.7 mg, 40% yield, 73% yield based on starting material consumed) as a white solid. M.p. 120°–125° C. (lit. m.p. 126°–7° C.). ¹H NMR (CDCl₃) 2.75 (2, H, m, CH₂S, 3.95–4.3 (2H, m, CHN, 4.3–4.9 (4H, two ab-q, PhCH), 7.25 (10H, s, arom), IR (CHCl₃), 1800, 1700 cm⁻¹; mass spectrum, m/e (relative intensity) 338 (17), 187 (33), 91 (100).

In accordance with the above procedure but where there is used as starting material in place of the dibenzylimidazolone, any of the corresponding dilower alkyl or di(phenyllower alkyl) imidazolones produced in accordance with example 6, there are produced the corresponding imidazolones.

We claim:

1. A compound of formula

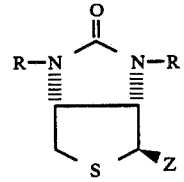

wherein R is benzyl and Z is halo.

2. A compound of claim 1 being (3aα,4β,6aα)-1,3-Dibenzyl-4-chlorohexahydro-1H-thieno[3,4-d]imidazol-2(3H)-one.

* * * * *